US00PP35523P2

(12) United States Plant Patent
Blom

(10) Patent No.: US PP35,523 P2
(45) Date of Patent: Dec. 5, 2023

(54) ***CHRYSANTHEMUM* PLANT NAMED 'ZANMUROAR'**

(50) Latin Name: ***Chrysanthemum* X *morifolium***
Varietal Denomination: Zanmuroar

(71) Applicant: Wilhelmus Bernardus Blom, Leimuiden (NL)

(72) Inventor: Wilhelmus Bernardus Blom, Leimuiden (NL)

(73) Assignee: VAN ZANTEN BREEDING B.V., Rijsenhout (NL)

( * ) Notice: Subject to any disclaimer, the term of this patent is extended or adjusted under 35 U.S.C. 154(b) by 0 days.

(21) Appl. No.: 18/122,308

(22) Filed: Mar. 16, 2023

(51) Int. Cl.
*A01H 5/02* (2018.01)
*A01H 6/14* (2018.01)

(52) U.S. Cl.
USPC ..... Plt./293

(58) Field of Classification Search
USPC ..... Plt./284, 287, 293
See application file for complete search history.

*Primary Examiner* — Susan McCormick Ewoldt
(74) *Attorney, Agent, or Firm* — C. Anne Whealy

(57) ABSTRACT

A new and distinct cultivar of *Chrysanthemum* plant named 'Zanmuroar', characterized by its upright, outwardly spreading and uniformly spherical plant habit; moderately vigorous growth habit and moderate growth rate; freely branching habit; dense and full plant habit; early and freely flowering habit; long flowering period; decorative-type inflorescences with ray florets that are dark red in color; and good garden performance.

2 Drawing Sheets

Figure 1:
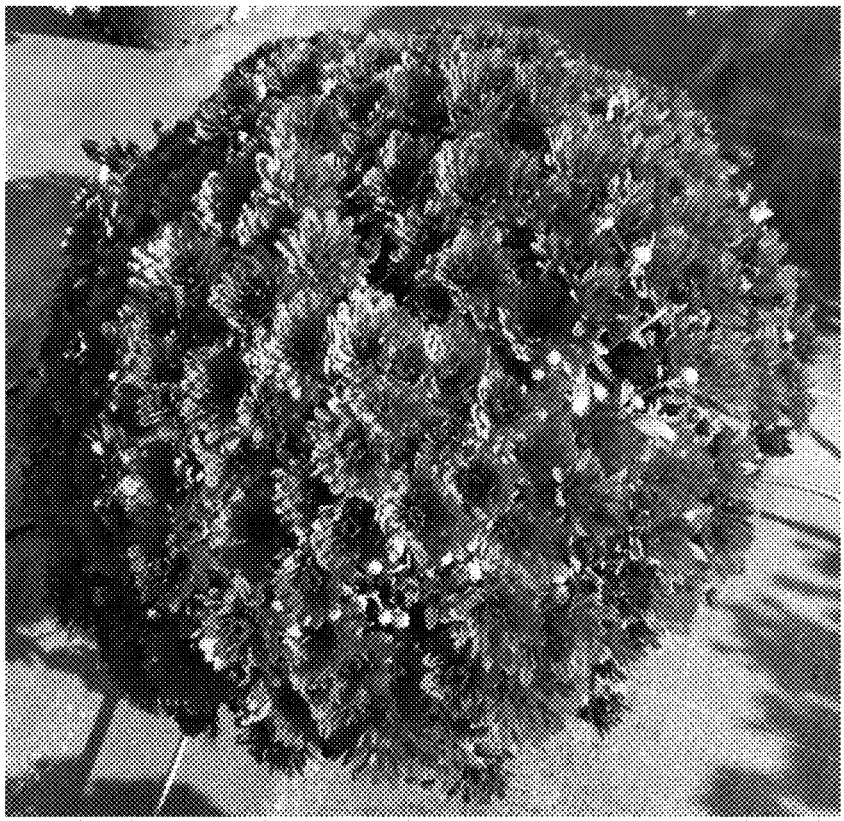

Botanical designation: *Chrysanthemum* X *morifolium*.
Cultivar denomination: 'ZANMUROAR'.

BACKGROUND OF THE INVENTION

The present invention relates to a new and distinct cultivar of *Chrysanthemum* plant, botanically known as *Chrysanthemum* X *morifolium*, commercially referred to as a Garden Mum and hereinafter referred to by the name 'Zanmuroar'.

The new *Chrysanthemum* plant is a product of a planned breeding program conducted by the Inventor in Rijsenhout, The Netherlands. The objective of the breeding program is to create new uniform spherically-shaped and early flowering *Chrysanthemum* plants with decorative-type inflorescences and attractive ray floret coloration.

The new *Chrysanthemum* plant originated from a cross-pollination in November, 2015 of a proprietary selection of *Chrysanthemum* x *morifolium* identified as code number 13-0323, not patented, as the female, or seed, parent with a proprietary selection of *Chrysanthemum* x *morifolium* identified as code number 13-0328, not patented, as the male, or pollen, parent. The new *Chrysanthemum* plant was discovered and selected as a single flowering plant from within the progeny of the stated cross-pollination in a controlled greenhouse environment in Rijsenhout, The Netherlands in July, 2016.

Asexual reproduction of the new *Chrysanthemum* plant by vegetative terminal cuttings was first conducted in a controlled greenhouse environment in Rijsenhout, The Netherlands since September, 2016. Asexual reproduction by vegetative terminal cuttings has shown that the unique features of this new *Chrysanthemum* plant are stable and reproduced true to type in successive generations.

SUMMARY OF THE INVENTION

The following traits have been repeatedly observed and are determined to be the unique characteristics of 'Zanmuroar'. These characteristics in combination distinguish 'Zanmuroar' as a new and distinct *Chrysanthemum* plant:

1. Upright, outwardly spreading and uniformly spherical plant habit.
2. Moderately vigorous growth habit and moderate growth rate.
3. Freely branching habit; dense and full plant habit.
4. Early and freely flowering habit.
5. Long flowering period.
6. Decorative-type inflorescences with ray florets that are dark red in color.
7. Good garden performance.

Plants of the new *Chrysanthemum* can be compared to plants of the female selection parent. Plants of the new *Chrysanthemum* differ primarily from plants of the female parent selection in ray floret color as ray florets of plants of the new *Chrysanthemum* are darker and more purplish red in color than ray florets of plants of the female parent selection.

Plants of the new *Chrysanthemum* can be compared to plants of the male selection parent. Plants of the new *Chrysanthemum* differ primarily from plants of the male parent selection in ray floret color as ray florets of plants of the new *Chrysanthemum* are darker red in color than ray florets of plants of the male parent selection.

Plants of the new *Chrysanthemum* can also be compared to plants of *Chrysanthemum* X *morifolium* 'Zanmufive', disclosed in U.S. Plant Pat. No. 19,791. In side-by-side comparisons, plants of the new *Chrysanthemum* differ primarily from plants of 'Zanmufive' in the following characteristics:

1. Plants of the new *Chrysanthemum* are smaller than plants of 'Zanmufive'.
2. Ray florets of plants of the new *Chrysanthemum* are darker red in color than ray florets of plants of 'Zanmufive'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1) is a top perspective view of a typical flowering plant of 'Zanmuroar' grown in a container.

Figure 2:
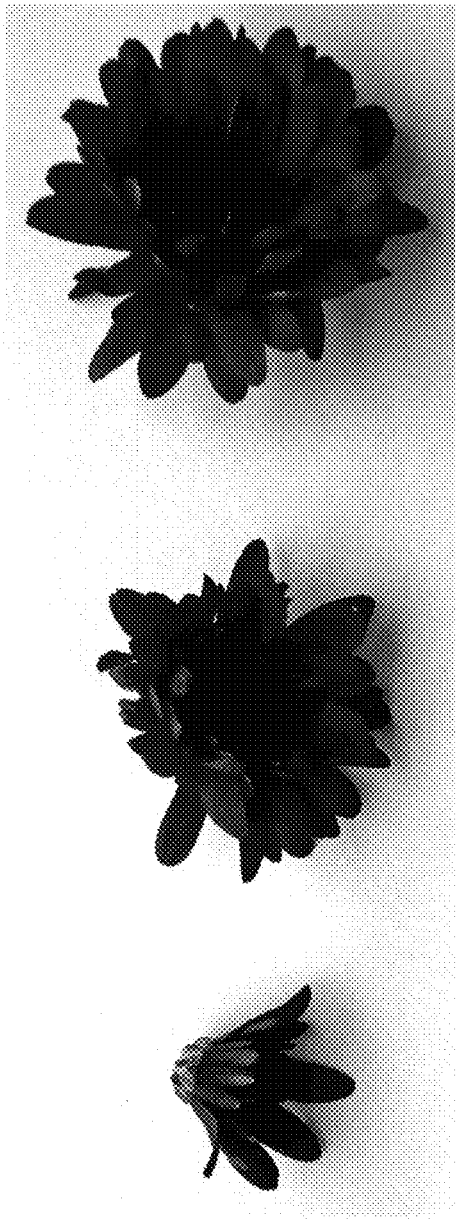

The photograph on the second sheet (FIG. 2) is a close-up view of developing and fully developed inflorescences from typical flowering plants of 'Zanmuroar'.

DETAILED BOTANICAL DESCRIPTION

The aforementioned photographs and following observations and measurements describe plants grown in 17-cm containers in an outdoor nursery in Rijsenhout, The Netherlands under natural daylengths during the summer and autumn and under cultural practices generally used in commercial *Chrysanthemum* production. During the production of the plants, day temperatures ranged from 15C to 25C and night temperatures ranged from 8C to 15C. Plants were 16 weeks from planting when the photograph was taken and the detailed description was taken on plants from 14 to 20 weeks after planting. In the following description, color references are made to The Royal Horticultural Society Colour Chart, 2015 Edition, except where general terms of ordinary dictionary significance are used.

Botanical classification: *Chrysanthemum* X *morifolium* 'Zanmuroar'.

Parentage:

*Female, or seed, parent*.—Proprietary selection of *Chrysanthemum* X *morifolium* identified as code number 13-0323, not patented.

*Male, or pollen, parent*.—Proprietary selection of *Chrysanthemum* X *morifolium* identified as code number 13-0328, not patented.

Propagation:

*Type cutting*.—By vegetative tip cuttings.

*Time to initiate roots, summer*.—About six to eight days at temperatures about 12C to 23C.

*Time to produce a rooted young plant, summer*.—About 12 to 13 days at temperatures about 12C to 23C.

*Root description*.—Thin, fibrous; typically close to 164D in color; actual color of the roots is dependent on substrate composition, water quality, fertilizer type and formulation, substrate temperature and physiological age of roots.

*Rooting habit*.—Freely branching; dense.

Plant description:

*Appearance*.—Perennial decorative-type *Chrysanthemum*; stems upright and outwardly spreading giving a uniformly rounded appearance to the plant; plants spherical in overall shape; very freely branching habit, about six to seven primary lateral branches develop, each primary lateral branch with about eight to nine secondary branches; dense, bushy and full plant habit; moderately vigorous growth habit and moderate growth rate.

*Plant height*.—About 28 cm to 30 cm.

*Plant width*.—About 40 cm.

*Lateral branches*.—Length: About 15 cm to 18 cm. Diameter: About 2 mm. Internode length: About 1.5 cm to 2 cm. Strength: Moderately strong. Aspect: About 30 to 45 degrees from vertical. Texture and luster: Pubescent; longitudinally ridged; matte. Color: Close to 138B; with development, becoming closer to 199D.

*Leaves*.—Arrangement: Alternate, simple. Length: About 2 cm to 6 cm. Width: About 0.5 cm to 3.5 cm. Shape: Elliptic to broadly elliptic. Apex: Acute, pointed. Base: Attenuate. Margin: Palmately lobed, sinuses between lateral lobes divergent and deep. Texture and luster, upper surface: Pubescent; slightly glossy. Texture and luster, lower surface: Pubescent; matte. Venation: Palmate and pinnate. Color: Developing and fully expanded leaves, upper surface: Close to 136A; venation, close to 147D. Developing and fully expanded leaves, lower surface: Close to 136C; venation, close to 148D. Petioles: Length: About 5 mm to 11 mm. Diameter: About 1.5 mm. Strength: Moderately strong. Texture and luster, upper and lower surfaces: Pubescent; matte. Color, upper surface: Close to 147D. Color, lower surface: Close to 148D.

Inflorescence description:

*Appearance*.—Decorative-type inflorescence form; inflorescences borne on terminals above foliar plane; ray florets arranged acropetally on a capitulum; inflorescences facing upright to outwardly.

*Fragrance*.—Fragrant, pungent and aromatic.

*Flowering response*.—Early flowering habit and long flowering period; under natural season conditions, plants flower from weeks 35/36 to week 40 in The Netherlands.

*Postproduction longevity*.—Inflorescences maintain good color and substance for about three weeks in an outdoor nursery; inflorescences persistent.

*Quantity of inflorescences*.—Freely flowering habit; about 240 to 260 inflorescences develop per plant.

*Inflorescence buds*.—Height: About 6 mm. Diameter: About 6 mm. Shape: Rounded. Texture and luster: Pubescent; slightly glossy. Color: Close to 138A to 138B.

*Inflorescence diameter*.—About 5 cm.

*Inflorescence depth* (*height*).—About 2.5 cm.

*Disc diameter*.—About 8 mm; inconspicuous.

*Receptacle diameter*.—About 4 mm.

*Receptacle height*.—About 3 mm.

*Receptacle shape*.—Domed.

*Receptacle color*.—Close to 138D.

*Ray florets*.—Number of ray florets per inflorescence: About 180 to 200 ray florets arranged in about ten whorls. Length, developing: About 1.2 cm. Length, developed: About 2 cm to 2.8 cm. Width, developing: About 2 mm. Width, developed: About 4 mm. Shape, developing and developed: Elliptic. Apex, developing: Acute, pointed. Apex, developed: Emarginate. Base, developing and developed: Attenuate. Margin, developing and developed: Entire; not undulate. Aspect, developing and developed: Mostly flat. Texture and luster, developing and developed, upper surface: Smooth, glabrous; slightly glossy. Texture and luster, developing and developed, lower surface: Smooth, glabrous; matte. Color: When opening, upper surface: Close to 187B. When opening, lower surface: Close to 184A. Fully opened, upper surface: Close to 185A; venation, close to 185A; color becoming closer to 182B with subsequent development. Fully opened, lower surface: Close to 181A; venation, close to 181A; color becoming closer to 182C with subsequent development.

*Disc florets*.—Number of disc florets per inflorescence: About 20 disc florets massed at the center of the receptacle. Length: About 4 mm. Width: About 1.5 mm. Shape: Tubular, elliptic. Apex: Dentate. Base: Attenuate and fused. Margin: Entire. Aspect: Mostly upright. Texture, upper and lower surfaces: Smooth, glabrous. Color: When opening and fully opened, upper surface: Close to 145C; towards the apex, close to 11D. When opening and fully opened, lower surface: Close to 145C; towards the apex, close to 11D.

*Phyllaries*.—Number of phyllaries per inflorescence: About 18 to 21 phyllaries arranged in about three whorls. Length: About 4 mm. Width: About 1.5 mm. Shape: Elliptic. Apex: Acute, pointed. Base: Attenuate. Margin: Entire. Texture and luster, upper surface: Smooth, glabrous; glossy. Texture and luster, lower surface: Pubescent; matte. Color, upper surface: Close to 143A. Color, lower surface: Close to 138A.

*Peduncles*.—Length, terminal peduncle: About 5 cm. Length, third peduncle: About 2.5 cm. Diameter, terminal peduncle: About 2 mm. Diameter, third peduncle: About 1 mm. Strength: Moderately strong. Aspect, terminal peduncle: Mostly upright. Aspect, third peduncle: About 30 degrees from lateral branch axis. Texture and luster: Pubescent; matte. Color: Close to 138B.

*Reproductive organs*.—Androecium: Not observed. Gynoecium: Number of pistils per ray floret: One. Pistil length: About 3 mm. Style length: About 2.5 mm. Style color: Close to 149C. Stigma diameter: About 1 mm. Stigma shape: Forked. Stigma color: Close to 12A. Ovary color: Close to 149C.

*Seeds and fruits*.—To date, seed and fruit production have not been observed on plants of the new *Chrysanthemum*.

Garden performance: Plants of the new *Chrysanthemum* have demonstrated good garden performance and will tolerate temperatures ranging from about 4C to about 30C.

It is claimed:

1. A new and distinct *Chrysanthemum* plant named 'Zanmuroar' as illustrated and described.

* * * * *